US00PP09615P

United States Patent [19]

Leue

[11] Patent Number: Plant 9,615

[45] Date of Patent: Jul. 30, 1996

[54] IMPATIENS PLANT NAMED 'LAVENDER ORCHID'

[75] Inventor: Ellen F. Leue, West Chicago, Ill.

[73] Assignee: Geo. J. Ball, Inc., West Chicago, Ill.

[21] Appl. No.: 445,376

[22] Filed: May 19, 1995

[51] Int. Cl.[6] ..... A01H 5/00

[52] U.S. Cl. ..... Plt./87.6

[58] Field of Search ..... Plt./87.6

*Primary Examiner*—Howard J. Locker

*Attorney, Agent, or Firm*—Burns, Doane, Swecker & Mathis, L.L.P.

[57] ABSTRACT

A new and distinct cultivar of Impatients plant, botanically known as *Impatiens wallerana*, and named 'Lavender Orchid' is provided. This new cultivar was the result of a controlled breeding program wherein a plant designated 359-1 (non-patented in the United States). The new cultivar is early blooming and forms in abundance attractive fully double lavender blooms that commonly include darker centers. The foliage is medium green. The plant exhibits a good basal-branching character and exhibits an upright mounded growth habit. The new cultivar can be readily distinguished from the 'Rosebud Lavender' cultivar (non-patented in the United States) in view of its larger flowers and larger leaves.

1 Drawing Sheet

SUMMARY OF THE INVENTION

The present invention provides a new and distinctive Impatiens plant, botanically known as *Impatiens wallerana*, and hereinafter referred to by the cultivar name 'Lavender Orchid'.

The new cultivar is the product of a planned breeding program. More specifically, the breeding program which resulted in the production of the new cultivar was carried out in a controlled environment during June, 1991 at Elburn, Ill., U.S.A. The female parent (i.e., the seed parent) was a plant designated 359-1 (non-patented in the United States) which exhibits light pink semi-double flowers and medium green foliage. The male parent (i.e., the pollen parent) was a plant designated 170-1-3 (non-patented in the United States) which exhibits pink double flowers with medium green foliage. The parentage of the new cultivar can be summarized as follows:

359-1×170-1-3.

The seeds resulting from the above pollination were sown and plantlets were obtained which were physically and biologically different from each other. Selective study resulted in the identification of a single plant of the new cultivar. This plant had distinctive fully double lavender blooms and initially was designated 723-1.

It was found that the new cultivar of the present invention:

(a) exhibits in abundance attractive fully double lavender blooms with darker centers,
(b) is early blooming,
(c) forms medium green foliage,
(d) exhibits a good basal-branching character, and
(e) exhibits an upright mounded growth habit.

Asexual reproduction of the new cultivar by stem cuttings taken during September, 1993, and during October, 1994, at Elburn, Ill., U.S.A., has demonstrated that the characteristics of the new cultivar as herein described are firmly fixed and are retained through successive generations of such asexual propagation.

The 'Lavender Orchid' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Rosebud Lavender' cultivar (non-patented in the United States), it is found that the new cultivar exhibits larger flowers (e.g., a diameter of approximately 4.0 to 4.1 cm. vs. approximately 3.5×3.7 cm.), and larger leaves (e.g., approximately 5.0 to 5.3 cm.×approximately 3.6 to 3.7 cm. vs. approximately 4.0 to 5.0×approximately 2.5 to 3.0 cm.).

When plant material of the 'Lavender Orchid' cultivar is subjected to standard random amplified polymorphic DNA marker analysis (RAPD) using polymerase chain reaction (PCR) and a known unique set of DNA primers, it is found to exhibit a different fingerprint map when compared to that of 'Rosebud Lavender' cultivar which confirms its genetic distinctiveness.

Plants of the new cultivar will be marketed under the FIESTA trademark by Geo. J. Ball, Inc.

BRIEF DESCRIPTION OF THE PHOTOGRAPHS

The accompanying photographs show the new 'Lavender Orchid' cultivar with colors being as nearly true as it is reasonably possible to make the same in color illustrations of this character. The plant was being grown in a greenhouse at West Chicago, Ill., U.S.A.

FIG. 1—illustrates the general appearance of an overall plant as seen primarily from above.

FIG. 2—illustrates the general appearance of a typical floret.

DETAILED DESCRIPTION

Figure 1:
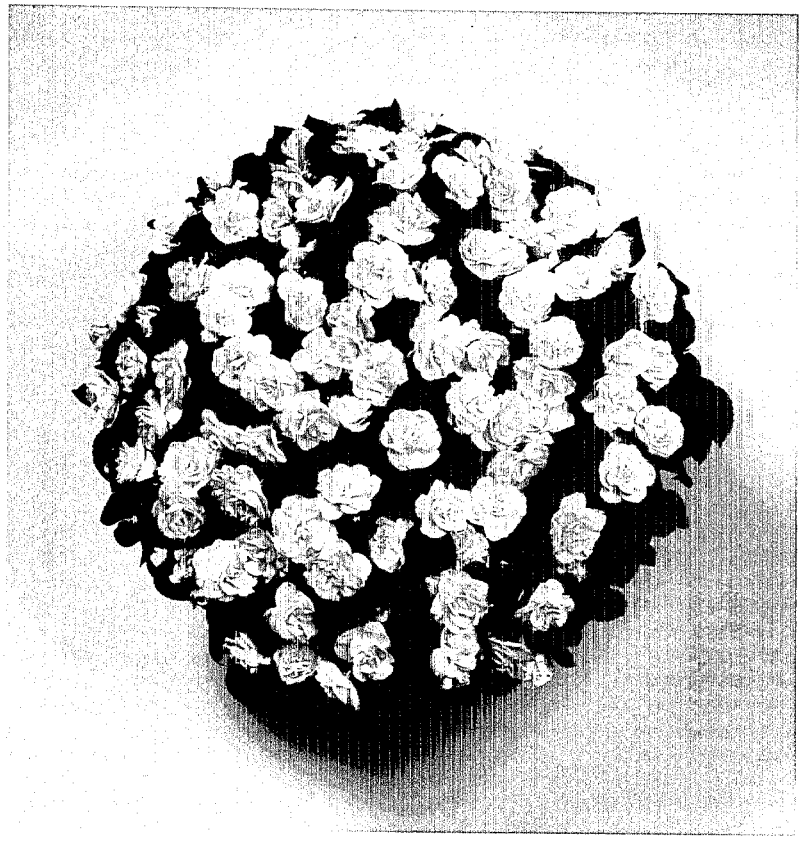
Figure 2:
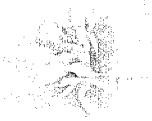

Th chart used in the identification of colors described herein is the R.H.S. Colour Chart of The Royal Horticultural Society, London, England. The color values were determined on Jan. 3, 1995. The readings were taken between 10:00 and 11:00 a.m. under 2,000 footcandles of light at West Chicago, Ill., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Two or three vegetative node stem cuttings from near the centers of the plants.

*Time to initiate roots.*—Approximately 7 to 14 days to the shorter times generally being experienced in the summer and the longer times in the winter.

*Rooting Habit.*—Fibrous, and branching.

Plant description:

*Habit of growth.*—Basal-branching, and exhibits a medium upright mounded growth habit.

*Form.*—A mature plant at 8 weeks after the planting of a rooted cutting commonly measures approximately 10.0 to 11.0 cm. in height and approximately 25.0 to 26.0 cm. in width compared to approximately 12.0 to 13.0 cm. in height and approximately 24.0 to 25.0 cm. in width for the 'Rosebud Lavender' cultivar.

*Foliage.*—The configuration is ovate with an acuminate tip. The leaves of the new cultivar commonly measure approximately 5.0 to 5.3 cm. in length and approximately 3.6 to 3.7 cm. in width while those of the 'Rosebud Lavender' cultivar commonly measure approximately 4.0 to 5.0 cm. in length and approximately 2.5 to 3.0 cm. in width. The foliage of the new cultivar is Green Group 137C (adaxial) and Green Group 138B (abaxial). This can be compared to Green Group 137A (adaxial) and Green Group 137C (abaxial) for the 'Rosebud Lavender' cultivar. The stem color is Yellow-Green Group 144C with streaks of Greyed-Purple Group 185A for both the 'Lavender Orchid' and the 'Rosebud Lavender' cultivars.

Flower description:

*Flowering habit.*—Freely flowering.

*Natural flowering season.*—Early blooming and blooms throughout the year in a greenhouse environment.

*Flowers borne.*—Slightly above the foliage.

*Flowers color.*—Purple Group 75B on fully opened petals with attachment points of Red-Purple Group 74A (adaxial) and Purple Group 75C (abaxial). This can be compared to Purple Group 75C (adaxial) and Purple Group 75D (abaxial) for the 'Rosebud Lavender' cultivar.

*Quantity of flowers.*—Extremely floriferous. A mature plant commonly is totally covered with blooms.

*Numbers of petals.*—Fully double and the petals commonly are too numerous to readily count.

*Flower size.*—Approximately 4.0 to 4.1 cm. in diameter. This can be compared to a diameter of approximately 3.5 to 3.7 cm. for the 'Rosebud Lavender' cultivar.

*Spur.*—One per flower of approximately 3.0 to 3.1 cm. in length and slightly curved. This can be compared to a length of approximately 3.4 to 3.5 cm. with little or no curvature for the 'Rosebud Lavender' cultivar.

*Spur color.*—Yellow-Green Group 144D for both the 'Lavender Orchid' and the 'Rosebud Lavender' cultivars.

*Reproductive organs.*—The stamens are multiple in number and the styles and ovaries are generally typical of the species and non-distinctive.

I claim:

1. A new and distinct cultivar of *Impatiens wallerana* plant named 'Lavender Orchid' substantially as herein shown and described, which:

(a) exhibits in abundance attractive fully double lavender blooms with darker centers,
(b) is early blooming,
(c) forms medium green foliage,
(d) exhibits a good basal-branching character, and
(e) exhibits an upright mounded growth habit.

* * * * *